United States Patent [19]

Urbach et al.

[11] Patent Number: 5,011,940

[45] Date of Patent: Apr. 30, 1991

[54] PROCESS FOR THE PREPARATION OF BICYCLIC AMINO CARBOXYLIC ACIDS, INTERMEDIATES IN THIS PROCESS, AND THEIR USE

[75] Inventors: Hansjörg Urbach, Taunus; Rainer Henning, Hattersheim am Main, both of Fed. Rep. of Germany

[73] Assignee: Hoechst Aktiengesellschaft, Frankfurt am Main, Fed. Rep. of Germany

[21] Appl. No.: 214,457

[22] Filed: Jul. 1, 1988

[30] Foreign Application Priority Data

Jul. 3, 1987 [DE] Fed. Rep. of Germany ....... 3722007

[51] Int. Cl.$^5$ .......................................... C07D 209/02
[52] U.S. Cl. ...................................................... 548/452
[58] Field of Search ......................................... 548/452

[56] References Cited

U.S. PATENT DOCUMENTS

| | | | |
|---|---|---|---|
| 4,374,847 | 2/1983 | Gruenfeld | 514/415 |
| 4,508,729 | 4/1985 | Vincent et al. | 514/419 |
| 4,525,301 | 6/1985 | Henning et al. | 260/112.5 R |
| 4,558,064 | 12/1985 | Teetz et al. | 514/409 |
| 4,558,065 | 12/1985 | Urbach et al. | 544/412 |
| 4,562,202 | 12/1985 | Urbach et al. | 514/423 |
| 4,587,258 | 5/1986 | Gold et al. | 514/18 |
| 4,591,598 | 5/1986 | Urbach et al. | 514/412 |
| 4,614,805 | 9/1986 | Urbach et al. | 548/427 |
| 4,620,012 | 10/1986 | Henning et al. | 548/411 |
| 4,659,838 | 4/1987 | Lerch | 548/452 |
| 4,668,796 | 5/1987 | Geiger et al. | 548/452 |
| 4,668,797 | 5/1987 | Urbach et al. | 548/452 |
| 4,684,662 | 8/1987 | Henning et al. | 548/452 |
| 4,691,022 | 9/1987 | Henning et al. | 548/408 |
| 4,714,708 | 12/1987 | Urbach et al. | 514/412 |
| 4,727,160 | 2/1988 | Teetz et al. | 548/452 |
| 4,808,573 | 2/1989 | Gold et al. | 514/19 |
| 4,818,749 | 4/1989 | Gold et al. | 514/19 |
| 4,822,894 | 4/1989 | Geiger et al. | 548/252 |
| 4,831,157 | 5/1989 | Gold et al. | 548/452 |

FOREIGN PATENT DOCUMENTS

| | | |
|---|---|---|
| 0012845 | 7/1980 | European Pat. Off. . |
| 0018549 | 11/1980 | European Pat. Off. . |
| 0037231A2 | 10/1981 | European Pat. Off. . |
| 0046953 | 3/1982 | European Pat. Off. . |
| 0049658 | 4/1982 | European Pat. Off. . |
| 0050800A1 | 5/1982 | European Pat. Off. . |
| 0050850A1 | 5/1982 | European Pat. Off. . |
| 0079022 | 5/1983 | European Pat. Off. . |
| 0090362 | 10/1983 | European Pat. Off. . |
| 0012401 | 3/1984 | European Pat. Off. . |
| 3322530 | 1/1985 | Fed. Rep. of Germany . |
| 813034 | 4/1981 | Finland . |
| 812859 | 3/1982 | Finland . |
| 813283 | 4/1982 | Finland . |
| 813422 | 5/1982 | Finland . |
| 2491469 | 4/1982 | France . |
| 64085 | 4/1981 | Israel . |
| 57-77672 | 5/1982 | Japan . |
| 57-112359 | 7/1982 | Japan . |
| 57-91974 | 8/1982 | Japan . |
| 198535 | 9/1984 | New Zealand . |
| 198702 | 8/1985 | New Zealand . |
| 81/5988 | 8/1982 | South Africa . |
| 83/2229 | 12/1983 | South Africa . |
| 2086390 | 5/1982 | United Kingdom . |
| 2095682 | 10/1982 | United Kingdom . |

OTHER PUBLICATIONS

Leonard et al., J. Am. Chem. Soc., 77, 439 (1955).
Cekovic, "Intramolecular Cyclization of Unsaturated Acyl Chlorides by Tributyltin Hydride", Tetrahedron Lett., 1972 (9), pp. 749–752.
Leonard et al., J. Am. Chem. Soc., 78, 3457 (1956).
Leonard et al., J. Am. Chem. Soc., 78, 3463 (1956).
Leonard et al., J. Am. Chem. Soc., 81, 5627 (1959).
Koelsch et al., J. Org. Chem. 26, 1104 (1961).
Griot et al., Helv. Chim. Acta, 42, 121 (1959).
Bonnett et al., J. Chem. Soc., 2087 (1959).
Battersby et al., J. Chem. Soc., 4333 (1958).
Rosenblatt et al., The Chemistry of Functional Groups, Supplement F: The Chemistry of Amino, Nitroso and Nitro Compounds and Their Derivatives. Part II, S. Patai, ed., Wiley & Sons: New York, 1982, pp. 1100–1104.
L. W. Haynes, Enamines, A. G. Cook, ed., Marcel Decker, Inc.: 1969, pp. 68–79, 261–269, 413.
Fieser & Fieser, Reagents for Organic Synthesis, vol. 1, pp. 644–651 (1967).
Boehme et al., Iminium Salts in Organic Chemistry, Part I (E. C. Taylor, ed.), Wiley & Sons: New York, 1976, p. 143.
S. Dayagi et al., The Chemistry of Functional Groups, The Chemistry of the Carbon–Nitrogen Double Bond, S. Patai, ed., Wiley & Sons: New York, 1970, p. 119.
W. Greenlee et al., J. Med. Chem., 28, 434–442 (1985).
K. Ogawa et al., J. Chem. Soc., Perkin Trans. I, 3031–3035 (1982).
R. Bacon and D. Stewart, J. Chem. Soc. (C), 1384–1387 (1966).
R. Bacon et al., J. Chem. Soc. (C), 1388–1389 (1966).
Patchett et al., Nature, 288, 280–283 (1980).
Booth et al., Chemistry and Industry, 466–467 (1956).
Booth et al., J. Chem. Soc., Part I, 1050–1054 (1959).
Murakoshi et al., Chemical Abstracts, 61, 9465(e) (1964).
Cushman et al., Fed. Proc., 38 (13), 2778–2782 (1979).
Houben-Weyl, Methoden der Organischen Chemie, 7(2b), 1403–1404 (1976).
Katritskaya, Dzh. Lagorskaya Khimia Geterosikl. Soedin., Moskow 1963, pp. 155–158.
Anderson, Jr., et al., J. Org. Chem., 43(1), 54–57 (1978).
Bertho et al., "Synthesen In Der 2-Azabicyclo[0.3.-3]-octan-Reihe", Chemische Berichte, 92(7), 2218–2235 (1959).
Farkas et al., J. Org. Chem., 22, 1261–1263 (1957).
Taylor et al., J. Org. Chem., 38(16), 2817–2821 (1973).
Taylor et al., Heterocycles, 25, 343–345 (1987).
English Language Translation of Mitzlaff et al., Liebig's Ann. Chem., 1713–1733 (1978).
Chem. Berichte 86: 1524–1528 (1953).
Quarterly Reviews 25: 323–341 (1971).
Chem. Abst. 49/1955/3009c.

United States Patent Office

PTO – BOYERS, PA Duty Station

MISSING PAGE TEMPORARY NOTICE

PATENT # __5011940__     FOR ISSUE DATE __4-30-91__

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

__Cont. Bib and Abst. Pg.__

N/a at Boyers
7/30/92

Data Conversion Operation
Boyers, Pa

PROCESS FOR THE PREPARATION OF BICYCLIC AMINO CARBOXYLIC ACIDS, INTERMEDIATES IN THIS PROCESS, AND THEIR USE

Acyl derivatives of octahydroindole-2-carboxylic acid, of octahydrocyclopenta[b]pyrrole-2-carboxylic acid and of decahydrocyclohepta[b]pyrrole-2-carboxylic acid are disclosed in, for example, EP-A 79022, EP-A 50800, EP-A 84164, EP-A 111873, EP-A 37231, U.S. Pat. No. 4,350,704 or U.S. Pat. No. 4,587,258. Many of these compounds show a remarkable biological activity. For example, they are highly effective inhibitors of angiotensin converting enzyme or are distinguished by a nootropic action.

Compounds of the formula I

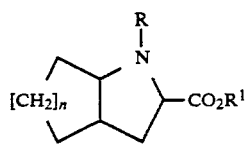

in which n=1-3, R denotes hydrogen or an acyl radical, and $R^1$ denotes hydrogen, an esterifying group or another carboxyl protective group, play a key role in the synthesis of the acyl derivatives mentioned at the outset.

It is often advantageous for the carbon atom in position 2 of the bicyclic ring system of these active substances to have a particular absolute configuration, preferably the S configuration. Hence, the synthesis thereof preferably starts from intermediates of the formula I which already have this desired configuration at C-2.

A racemate resolution has been indispensable in some of the known processes for the preparation of compounds of the formula I if the intention was to obtain compounds having a defined configuration at C-2.

Tetrahedron Letters 1987 1413–1416 discloses a process using which it is possible, in a synthesis starting from L-aspartic acid and totaling 12 stages, to obtain optically pure octahydroindole derivatives having a defined configuration at C-2.

It has now been found that appropriately substituted serine derivatives can be converted by cyclization into optically pure compounds of the formula I having the desired configuration at C-2 without there being the necessity for racemate resolution at any stage in this new process.

The invention relates to a process for the preparation of compounds of the formula I in which n = 1, 2 or 3, R denotes $(C_1-C_{14})$-acyl and $R^1$ denotes $(C_1-C_6)$-alkyl, $(C_3-C_7)$-cycloalkyl, $C_7-C_{11}$)-aralkyl or another carboxyl protective group, the configuration of the hydrogen atoms at the bridgehead carbon atoms 3a and (5+n)a preferably being cis, which comprises radical cyclization of compounds of the formula II

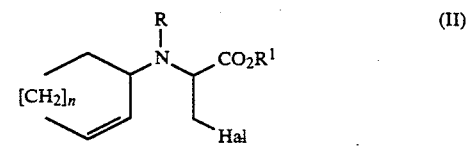

in which n, R and $R^1$ are as defined above, and Hal denotes chlorine, bromine or iodine.

As shown by the following scheme, using the process according to the invention and starting from, for example, 3-bromocyclopentene (V) and L-serine (III), the optically pure diastereomers Ia and Ib, which are homologs of the abovementioned octahydroindole derivatives, are obtained in a synthesis totaling only 7 stages. In fact, the number of stages in the process is reduced by one stage to a total of 6 stages if it is carried out via the stage of L-serine benzyl ester.

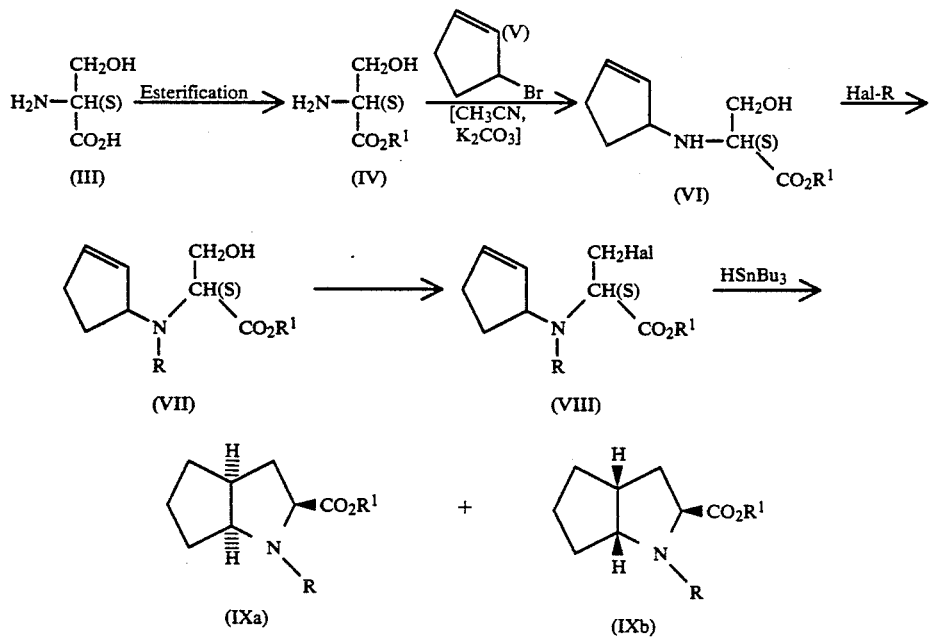

Scheme

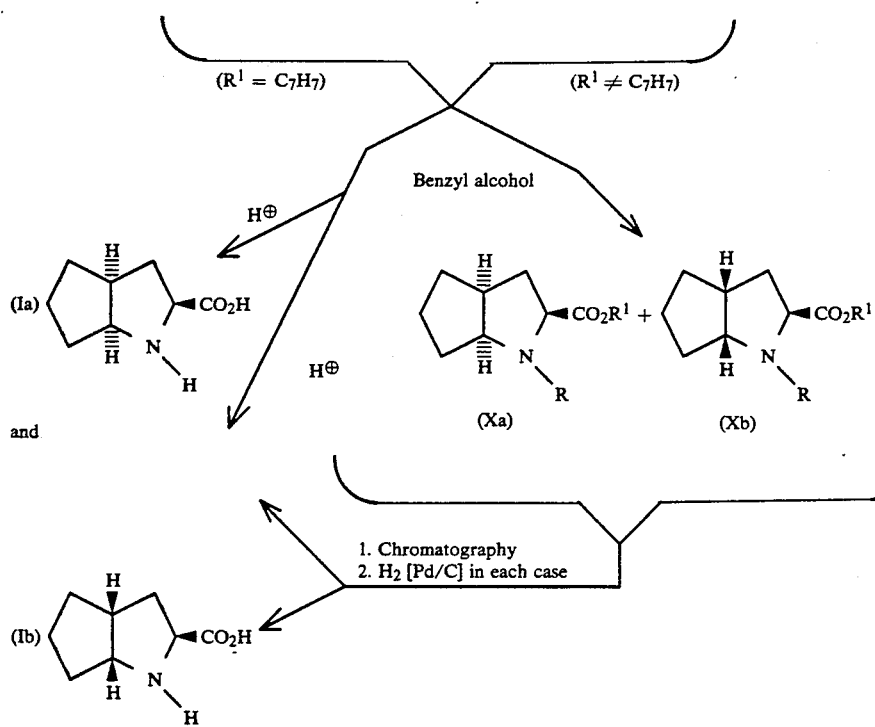

Both the R and S configuration are possible for the carbon atom in position 2 of the bicyclic ring system of the compounds of the formulae I and II; the S configuration is preferred.

R is preferably $(C_1-C_6)$-alkanoyl, $(C_6-C_{10})$-aryl-$(C_1-C_4)$-alkanoyl, $(C_6-C_{10})$-aroyl, $(C_1-C_6)$-alkoxycarbonyl or $(C_7-C_{11})$-aralkyloxycarbonyl, but is in particular $(C_1-C_4)$-alkanoyl, such as acetyl or propionyl, benzoyl or substituted benzoyl, such as, for example, halogenobenzoyl, methoxybenzoyl, dimethoxybenzoyl or nitrobenzoyl.

Furthermore, if not already covered by the abovementioned definitions, R can represent an amine protective group of the urethane type customary in peptide chemistry (cf. for example, Hubbuch, Kontakte Merck 3/79, 14–22). Examples of protective groups of the urethane type are Pyoc, Fmoc, Tcboc, Z, Boc, Ddz, Bpoc, Adoc, Msc, Moc, Z(N02), Z(Haln), Dobz, Iboc, Adpoc, Mboc and 1,4-dimethylpyridyloxycarbonyl.

$R^1$ is preferably $(C_1-C_4)$-alkyl such as, for example, methyl, ethyl or tert.-butyl, or $(C_7-C_{11})$-aralkyl such as, for example, benzyl.

Furthermore, if not already covered by the abovementioned definitions, $R^1$ can represent a carboxyl protective group customary in peptide chemistry (cf., for example, the abovementioned article by Hubbuch), for example the abovementioned alkyl radicals or benzyl. Also suitable are modified benzyl radicals such as p-nitrobenzyl, p-methoxybenzyl, p-bromobenzyl and p-chlorobenzyl, and radicals such as 4-picolyl or benzoylmethyl.

Alkyl is to be understood hereinbefore and hereinafter as straight-chain or branched alkyl. A corresponding statement applies to radicals derived therefrom, such as, for example, alkanoyl and aralkyl. Lower alkyl preferably has up to 6 carbon atoms. Examples of $(C_6-C_{10})$-aryl are phenyl and naphthyl; phenyl is preferred. A corresponding statement applies to radicals derived therefrom, such as, for example, aroyl and aralkyl.

The radical cyclization can be carried out, for example, with trialkylstannanes such as, for example, with tri-nbutyltin hydride, in a suitable solvent between $-20°$ C. and $120°$ C., preferably between $0°$ C. and the boiling point of the reaction mixture, in particular at the boiling point, where appropriate in the presence of a radical initiator. Particularly suitable solvents for this are aprotic solvents such as benzene, toluene or xylene. Examples of suitable initiators are organic peroxides such as tert.-butyl peroxide, substituted azobis(alkanenitriles) such as, for example, 2,2'-azoisobutyronitrile (AIBN), mercaptans and stannanes; AIBN is preferred.

Furthermore, the radical cyclization can be carried out in a suitable dipolar aprotic solvent between $-20°$ C. and the boiling point of the reaction mixture, preferably between $10°$ and $50°$ C. Examples of suitable dipolar aprotic solvents are ethers such as diethyl ether, tetrahydrofuran and dioxane.

The compounds of the formula II are prepared starting from cycloalkenyl bromides of the formula XI

(XI)

in which n is 1, 2 or 3. These are reacted with serine derivatives of the formula IV in which $R^1$ is as defined above and preferably denotes $(C_1-C_6)$-alkyl or $(C_7-C_{11})$aralkyl, such as methyl or benzyl, and which have the R or S, preferably S, configuration, in the presence of a base such as $K_2CO_3$, in a dipolar aprotic solvent such as acetonitrile, between $0°$ C. and the boiling point of the reaction mixture, preferably at room temperature, to give compounds of the formula XII

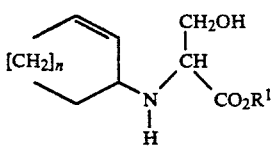

in which n and $R^1$ are as defined above.

Since the compound of the formula XII may be in the form of a mixture of diastereomers, this can, where appropriate, be separated into the pure diastereomers by salt formation and fractional crystallization or by chromatography. If the pure diastereomers are used in the reaction sequence, the separation of the diastereomers at a later stage is dispensed with, which then has a favorable effect on the overall yield.

Compounds of the formula XII are then acylated to give compounds of the formula XIII

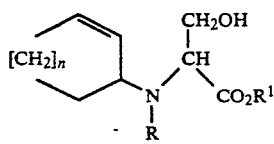

in which n, R and $R^1$ are as defined above. The acylation is expediently and preferably carried out in the presence of a base in a dipolar aprotic solvent such as acetone, between $-20°$ C. and the boiling point of the reaction mixture, preferably at room temperature. Examples of suitable acylating agents are the chlorides of the formula RCl or the anhydrides of the formula $R_2O$. Suitable bases are tert.-amines such as triethylamine, and inorganic bases such as $K_2CO_3$.

The reaction of the compounds of the formula XIII to give compounds of the formula II, in which n, R, $R^1$ and Hal are as defined above is expediently carried out in such a way that the hydroxyl group of the compounds of the formula XIII is replaced by a leaving group. Thus, it is possible to prepare by known processes, for example, the corresponding tosylates, mesylates or triflates, which can then be nucleophilically converted with chloride, bromide or iodide into the compounds of the formula II.

However, it is also possible to introduce chlorine directly, for example by reaction of the compounds of the formula XIII with $PCl_5$, and bromine by reaction of $PBr_3$, for example. The iodo compound of the formula II is expediently prepared from compounds of the formula XIII using triphenylphosphine and iodine in the presence of imidazole, preferably at room temperature, in an aprotic non-polar solvent such as, for example, benzene or toluene.

The invention also relates to the intermediates of the formula IIa

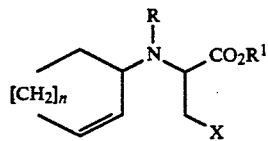

in which n denotes 1, 2 or 3,

X denotes hydroxyl, chlorine, bromine or iodine,

R denotes hydrogen or $(C_1-C_{14})$-acyl, and $R^1$ denotes $(C_1-C_6)$-alkyl, $(C_3-C_7)$-cycloalkyl, $(C_7-C_{11})$-aralkyl or another carboxyl protective group.

The examples which follow serve to illustrate the invention without intending to restrict it.

EXAMPLE 1

N-(2-Cyclopenten-1-yl)-L-serine methyl ester 48 g of solid $K_2CO_3$ are added to 24.5 g of L-serine methyl ester hydrochloride in 200 ml of dry acetonitrile. 23.2 g of isopentenyl bromide in carbon tetrachloride are added to this mixture while cooling in ice. The mixture is allowed to reach room temperature and is stirred at this temperature for 2 hours. The solid is filtered off with suction, and then the filtrate is concentrated, and the residue is chromatographed on silica gel using $CH_2Cl_2$ as eluent.

Yield: 7.6 g; melting point 113°–126° C.

$[\alpha]_D^{20}$: $-30.5°$ (c=1.13; $CH_3OH$)

EXAMPLE 2

N-(2-(1S)-Cyclopenten-1-yl)-L-serine methyl ester

The mixture of diastereomers from Example 1 is converted into the hydrochloride using ethanolic HCl in ethyl acetate (melting point 150°–160° C., $[\alpha]_D^{20}=10.9°$ (c=0.96; $CH_3OH$)), followed by recrystallization several times from dry acetonitrile.

The S,S compound (94% pure, as HCl salt) has an optical rotation of $[\alpha]_D^{20}=-67.5°$ (c=0.85; $CH_3OH$), melting point 180° C.

The free base is liberated from the hydrochloride using aqueous $K_2CO_3$ solution: $[\alpha]_D^{20}=-111.7°$ (c=0.86; $CH_3OH$).

EXAMPLE 3

N-(2-(1R)-Cyclopenten-1-yl)-L-serine methyl ester

The (R,S) compound is obtained (about 85% pure) as HCl salt in analogy to Example 2 by recrystallization of the hydrochloride in dry acetonitrile, ethyl acetate and $CH_2Cl_2$. Melting point 152°–154° C.; $[\alpha]_D^{20}=+82.78°$ (c=0.61; $CH_3OH$). $[\alpha]_D^{20}$ of the free base: $+38.3°$ (c=0.88; $CH_3OH$).

EXAMPLE 4

N-Benzyloxycarbonyl-N-(2-(1R,S)-cyclopenten-1-yl)-L-serine methyl ester 10.5 g of the methyl ester from Example 1 are suspended in 164 ml of saturated aqueous $NaHCO_3$ solution. 11.24 ml of benzyl chloroformate are added to this at room temperature. After stirring for 2 hours, the mixture is extracted with ethyl acetate. The organic phase is washed successively with 2N aqueous HCl, half-saturated aqueous $NaHCO_3$ solution, water and saturated aqueous NaCl solution. It is dried and then concentrated.

The residue is chromatographed on silica gel using $CH_2Cl_2$/ethyl acetate 95:5.

Yield: 14.4 g, $[\alpha]_D^{20}=-65°$ (c=1; $CH_3OH$).

EXAMPLE 5

Methyl 2-(S)-[N-benzyloxycarbonyl-N-(2-(1R,S)-cyclopenten-1-ylamino)]-3-iodopropionate 0.412 g of triphenylphosphine and 0.107 g of imidazole are introduced into 7 ml of dry benzene. 0.346 g of iodine in 3 ml of dry benzene is added dropwise to this at room temperature. After a yellow precipitate has separated out the mixture is stirred for 10 minutes. Then, at room temperature and protecting from light, 0.319 g of the alcohol from Example 4 in 2 ml of dry benzene is added dropwise. The mixture is stirred at room temperature for 3 hours. It is then poured onto ether/water. The ethereal solution is washed with water, dried and concentrated in a rotary evaporator. The residue is chromatographed on silica gel using cyclohexane/ethyl acetate 9:1. Yield: 0.2 g of oil; $R_f$: 0.65 ($SiO_2$; $CH_2Cl_2$/ethyl acetate 95:5; $I_2$).

EXAMPLE 6

Methyl N-benzyloxycarbonyl-(1S,3S,5S)-2-azabicyclo[3.3.0]octane-3-carboxylate and methyl N-benzyloxycarbonyl(1R,3S,5R)-2-azabicyclo[3.3.0]octane-3-carboxylate 3.25 g of the iodo compound from Example 5, 521 mg of azobisisobutyronitrile (AIBN) and 2.31 g of tri-n-butyltin hydride are dissolved in 260 ml of dry benzene. The solution is refluxed under nitrogen for 4 hours. It is then concentrated in a rotary evaporator, and the residue is taken up in ether. The ethereal solution is stirred with 10% strength aqueous KF solution for 30 minutes; the ethereal solution is filtered and then dried and concentrated in a rotary evaporator.

The residue is chromatographed on silica gel using cyclohexane/ethyl acetate 4:1. Yield: 2.0 g $[\alpha]_D^{20} = -40.5°$ (c=1.035; $CH_3OH$).

EXAMPLE 7

Benzyl N-benzyloxycarbonyl-(1R,3S,5R)-2-azabicyclo[3.3.0]octane-3-carboxylate 1 g of the mixture of diastereomers from Example 6 is dissolved in 10 ml of benzyl alcohol, 0.35 ml of titanium tetraisopropylate is added dropwise, and the mixture is stirred at 90° C. under oil pump vacuum for 4 hours. A further 1.6 ml of titanium tetraisopropylate are then added dropwise, and the mixture is stirred at 90° C. under oil pump vacuum for 6 hours. The benzyl alcohol is then removed in vacuo, the residue is taken up in ether, and the ether is washed with 2N aqueous HCl, then with saturated aqueous $NaHCO_3$ solution and, after the precipitate has been removed by filtration with suction, with saturated aqueous NaCl solution. Drying is followed by concentration in a rotary evaporator. The residue is chromatographed on silica gel using cyclohexyl/ethyl acetate 9:1. The product which eluted first is the (1R,3S,5R) compound (cis, exo configuration). Yield: 422 mg $[\alpha]_D^{20} = -101.6°$ (c=0.82; $CH_3OH$).

EXAMPLE 8

Benzyl N-benzyloxycarbonyl-(1S,3S,5S)-2-azabicyclo[3.3.0]octane-3-carboxylate The product from Example 7 which eluted after the cis,exo compound is the (1S,3S,5S) compound (cis,endo configuration).

Yield: 553 mg of oil (from the batch of Example 7). $[\alpha]_D^{20} = -2.8°$ (c=1.1; $CH_3OH$).

EXAMPLE 9

(1R,3S,5R)-2-Azabicyclo[3.3.0]octane-3-carboxylic acid 400 mg of the final product from Example 7 are dissolved in 10 ml of ethanol, 50 mg of Pd/C (10%) are added to this, and the mixture is hydrogenated for 6 hours.

The catalyst is removed by filtration with suction, the filtrate is concentrated, and the residue is stirred with ethyl acetate.

Yield: 90 mg; melting point 220°-225° C. $[\alpha]_D^{20} = -48.4°$ (c=0.37; $CH_3OH$).

EXAMPLE 10

(1S,3S,5S)-2-Azabicyclo[3.3.0]octane-3-carboxylic acid 500 mg from Example 8 are reacted in analogy to Example 9.

Yield: 186 mg; melting point 235°-238° C. $[\alpha]_D^{20} = -53°$ (c=0.52; $CH_3OH$).

We claim:

1. A process for the preparation of a compound of the formula I

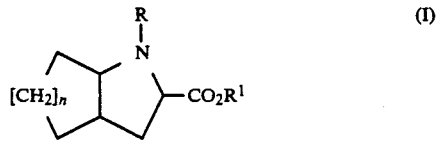

in which n=1, 2 or 3;

R denotes ($C_1$–$C_6$)-alkanoyl, ($C_6$–$C_{10}$)-aryl-($C_1$–$C_4$)-alkanoyl, ($C_6$–($C_{10}$)-aroyl, ($C_1$–$C_6$)-alkoxycarbonyl, ($C_7$–$C_{11}$)-aralkyloxycarbonyl or, if not covered by the above definition, R is a urethane type protecting grup selected from Pyoc (4-pyridylmethyloxycarbonyl), Fmoc (9-fluoroenylmethyloxycarbonyl), Tcboc (2,2,2-trichloro-t-butyloxycarbonyl), Z (benzyloxycarbonyl), Box (t-butyloxycarbonyl), Ddz (α,α-dimethyl3,5-dimethylybenzyloxycarbonyl), Bpoc (1-(4-biphenylyl)-1-methyl-ethyloxycarbonyl), Adoc (1-adamantyloxycarbonyl), Msc (methyl-sulfonyl-ethyloxycarbonyl), Moc (4-methyl-oxybenzyloxycarbonyl), Z($NO_2$) (4-nitrobenzyloxy-carbonyl), Z(Hal)$_n$ (halogenosubstituted benzyloxycarbonyl), Dobz (4-dihydroxyborylbenzyloxycarbonyl), Iboc (isobornyloxycarbonyl), Adpoc (1-(1-0adamantyl)-1-methyl-ethyloxycarbonyl), Mboc (1-methylcyclobutyloxy-carbonyl) and 1,4-dimethylpyridyloxycarbonyl; and $R^1$ denotes ($C_1$–$C_6$)-alkyl, ($C_3$–$C_7$)-cycloalkyl, ($C_7$–$C_{11}$)-aralkyl, p-nitrobenzyl, p-methoxybenzyl, p-bromobenzyl, p-chlorobenzyl, 4-picolyl or benzoylmethyl, which comprises radical cyclization of a compound of the formula II

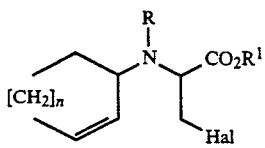

in which n, R and $R^1$ are as defined above, and Hal denotes chlorine, bromine or iodine with at least one trialkylstannane in an aprotic solvent at a temperature of from $-20°$ C. to $120°$ C.

2. The process as claimed in claim 1, in which the configuration of the hydrogen atoms at the bridgehead carbons 3a and (5+n)a is cis.

3. The process as claimed in claim 1, in which is cyclized a compound of the formula II in which $R^1$ denotes $(C_1-C_4)$-alkyl or $(C_7-C_{11})$-aralkyl.

4. The process as claimed in claim 1, wherein said trialkylstannane is tri-n-butyltin hydride.

5. The process as claimed in claim 1, wherein the aprotic solvent is benzene, toluene or xylene.

6. The process as claimed in claim 1, wherein the reaction is carried out between $0°$ C. and the boiling point of the reaction mixture.

7. The process as claimed in claim 1, wherein a radical initiator is used.

8. The process as claimed in claim 7, wherein the radical initiator is an organic peroxide.

9. The process as claimed in claim 7, wherein the radical initiator is selected from ter.-butyl peroxide, substituted azobis(alkaneitriles), mercaptans and stannanes.

10. The process as claimed in claim 7, wherein the radical initiator is 2,2'-azoisobutyronitrile (AIBN).

11. A process for the preparation of a compound of the formula I

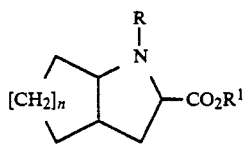

in which
n=1,2 or 3;
R denotes $(C_1-C_6)$-alkanoyl, $(C_6-C_{10})$-aryl-$(C_1-C_4)$-alkanoyl, $(C_6-(C_{10})$-aroyl, $(C_1-C_6)$-alkoxycarbonyl, $(C_7-C_{11})$-aralkyloxycarbonyl or, if not covered by the above definition, R is a urethane type protecting grup selected from Pyoc (4-pyridylmethyloxycarbonyl), Fmoc (9-fluoroenylmethyloxycarbonyl), Tcboc (2,2,2-trichloro-t-butyloxycarbonyl), Z (benzyloxycarbonyl), Box (t-butyloxycarbonyl), Ddz ($\alpha,\alpha$-dimethyl3,5-dimethyloxybenzyloxycarbonyl), Bpoc (1-(4-biphenylyl)-1-methylethyloxycarbonyl), Adoc (1-adamantyloxycarbonyl), Msc (methyl-sulfonyl-ethyloxycarbonyl), Moc (4-methyloxybenzyloxycarbonyl), $Z(NO_2)$ (4-nitrobenzyloxy-carbonyl), $Z(NO_2)$ (4-nitrobenzyloxycarbonyl), $Z(Hal)_n$ (halogenosubstituted benzyloxycarbonyl), Dobz (4-dihydroxyborylbenzyloxycarbonyl), Iboc (isobornyloxycarbonyl), Adpoc (1-(1-adamantyl)-1-methyl-ethyloxycarbonyl), Mboc (1-methylcyclobutyloxy-carbonyl) and 1,4-dimethylpyridyloxycarbonyl; and $R^1$ denotes $(C_1-C_6)$-alkyl, $(C_3-C_7)$-cycloalkyl, $(C_7-C_{11})$-aralkyl, p-nitrobenzyl, p-methoxybenzyl, p-bromobenzyl, p-chlorobenzyl, 4-picolyl or benzoylmethyl, which comprises radical cyclization of a compound of the formula II

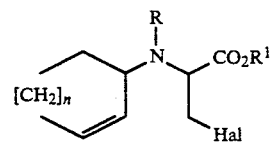

in which n, R and $R^1$ are as defined above, and Hal denotes chlorine, bromine or iodine with at least one trialkylstannane in an aprotic solvent at a temperature of from $-20°$ C. to the boiling point of the reaction mixture.

12. The process as claimed in claim 11, in which the configuration of the hydrogen atoms at the bridgehead carbons 3a and (5+n)a is cis.

13. The process as claimed in claim 11, wherein the dipolar aprotic solvent is an ether.

14. The process as claimed in claim 11, wherein the dipolar aprotic solvent is diethyl ether, tetrahydrofuran or dioxane.

15. The process as claimed in claim 11, wherein the reaction is carried out at a temperature of from $10°$ C. to $50°$ C.

16. The process as claimed in claim 11, wherein a radical initiator is used.

17. The process as claimed in claim 16, wherein the radical initiator is an organic peroxide.

18. The process as claimed in claim 16, wherein the radical initiator is selected from tert.-butyl peroxide, substituted azobis(alkanenitriles), mercaptans and stannanes.

19. The process as claimed in claim 16, wherein the radical initiator is 2,2'-azoisobutyronitrile (AIBN).

* * * * *

UNITED STATES PATENT AND TRADEMARK OFFICE
CERTIFICATE OF CORRECTION

PATENT NO. : 5,011,940
DATED : April 30, 1991
INVENTOR(S) : Hansjorg Urbach et al.

It is certified that error appears in the above-identified patent and that said Letters Patent is hereby corrected as shown below:

Claim 1, column 8, line 49, change "grup" to --group--.
Claim 1, column 8, line 52, change "Box" to --Boc--.
Claim 1, column 8, line 53, after "dimethyl" insert ----- (hyphen).
Claim 1, column 8, line 61, delete "O" before "adamantyl".
Claim 9, column 9, line 32, change "ter." to --tert.--.
Claim 9, column 9, line 34, change "alkaneitriles" to --alkanenitriles--.
Claim 11, column 9, line 50, change "($C_6$-($C_{10}$)-- to --($C_6$-$C_{10}$)--.
Claim 11, column 9, line 53, change "grup" to --group--.
Claim 11, column 10, line 1, change "Box" to --Boc--.
Claim 11, column 10, line 2, after "dimethyl" insert ----- (hyphen).
Claim 11, column 10, line 4, change "methylethyloxycarbonyl" to --methyl-ethyloxycarbonyl--.
Claim 11, column 10, line 7, delete "(4-nitrobenzyloxy-carbonyl), $Z(NO_2)$".

UNITED STATES PATENT AND TRADEMARK OFFICE
CERTIFICATE OF CORRECTION

PATENT NO. : 5,011,940
DATED : April 30, 1991
INVENTOR(S) : Hansjorg Urbach et al It is certified that error appears in the above-indentified patent and that said Letters Patent is hereby corrected as shown below:

Claim 11, column 10, line 31, delete "an" an insert --a dipolar--.

Signed and Sealed this

Twenty-ninth Day of June, 1993

Attest:

MICHAEL K. KIRK

*Attesting Officer*   Acting Commissioner of Patents and Trademarks